US011819672B2

(12) United States Patent
Nemoto et al.

(10) Patent No.: US 11,819,672 B2
(45) Date of Patent: Nov. 21, 2023

(54) CHEMICAL LIQUID INJECTOR

(71) Applicant: Nemoto Kyorindo Co., Ltd., Tokyo (JP)

(72) Inventors: Shigeru Nemoto, Tokyo (JP); Koji Yamaguchi, Tokyo (JP); Takahiro Moriyama, Tokyo (JP); Yoichi Sonoda, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 566 days.

(21) Appl. No.: 16/769,041

(22) PCT Filed: Dec. 6, 2018

(86) PCT No.: PCT/JP2018/044879
§ 371 (c)(1),
(2) Date: Jun. 2, 2020

(87) PCT Pub. No.: WO2019/111995
PCT Pub. Date: Jun. 13, 2019

(65) Prior Publication Data
US 2021/0228812 A1 Jul. 29, 2021

(30) Foreign Application Priority Data
Dec. 8, 2017 (JP) .................................. 2017-235796

(51) Int. Cl.
*A61M 5/315* (2006.01)
*A61M 5/00* (2006.01)
(Continued)

(52) U.S. Cl.
CPC ........ *A61M 5/31596* (2013.01); *A61M 5/007* (2013.01); *A61M 5/14566* (2013.01);
(Continued)

(58) Field of Classification Search
CPC .............. A61M 5/31596; A61M 5/007; A61M 5/14566; A61M 5/16877; A61M 5/1408;
(Continued)

(56) References Cited

U.S. PATENT DOCUMENTS

2004/0249344 A1* 12/2004 Nemoto .............. A61M 5/1458
604/151
2006/0079842 A1* 4/2006 Small ................ A61M 5/14546
600/432

(Continued)

FOREIGN PATENT DOCUMENTS

JP 2007-536005 A 12/2007
JP 2008-515603 5/2008
(Continued)

OTHER PUBLICATIONS

English translation of patent WO-2014168210-A1 (Year: 2014).*

(Continued)

*Primary Examiner* — Nilay J Shah
(74) *Attorney, Agent, or Firm* — Knobbe, Martens Olson & Bear, LLP

(57) ABSTRACT

A chemical liquid injector including a driving mechanism which applies a pressure to a chemical liquid in a container and pushes out the chemical liquid, and an injection control unit for setting operating conditions of the driving mechanism. The control unit has a main-injection condition determination section which determines injection conditions for a main injection, and an injection preliminary operation condition determination section which determines injection conditions for an injection preliminary operation, and is configured to execute the injection preliminary operation and the main injection consecutively in this order when injecting chemical liquid.

9 Claims, 10 Drawing Sheets

(51) Int. Cl.
*A61M 5/145* (2006.01)
*A61M 5/168* (2006.01)
*A61B 6/00* (2006.01)
*A61M 5/14* (2006.01)
*A61M 5/19* (2006.01)

(52) U.S. Cl.
CPC .......... *A61M 5/16877* (2013.01); *A61B 6/481* (2013.01); *A61M 5/1408* (2013.01); *A61M 5/19* (2013.01); *A61M 2005/14553* (2013.01); *A61M 2205/3334* (2013.01); *A61M 2205/502* (2013.01); *A61M 2206/16* (2013.01)

(58) Field of Classification Search
CPC ............ A61M 5/19; A61M 2205/3334; A61M 2206/16; A61M 2205/502
See application file for complete search history.

(56) References Cited

U.S. PATENT DOCUMENTS

| | | | | |
|---|---|---|---|---|
| 2006/0184122 | A1* | 8/2006 | Nemoto | A61M 5/16827 604/154 |
| 2007/0093712 | A1* | 4/2007 | Nemoto | A61M 5/14546 600/463 |
| 2007/0100282 | A1* | 5/2007 | Small | A61M 5/14566 700/282 |
| 2007/0167919 | A1* | 7/2007 | Nemoto | A61M 5/007 604/189 |
| 2012/0306881 | A1* | 12/2012 | Nemoto | G16H 40/63 345/440 |
| 2013/0030290 | A1* | 1/2013 | Nemoto | A61M 5/16827 600/432 |

FOREIGN PATENT DOCUMENTS

| | | | |
|---|---|---|---|
| JP | 2011-218194 A | 7/2011 | |
| JP | 5800713 B2 | 10/2015 | |
| WO | WO 2005/107419 | 11/2005 | |
| WO | WO 2005/107419 A2 | 11/2005 | |
| WO | WO 2006/044409 A2 | 4/2006 | |
| WO | WO 2014/0168210 | 10/2014 | |
| WO | WO 2014/168210 A1 | 10/2014 | |
| WO | WO-2014168210 A1 * | 10/2014 | .......... A61M 5/1407 |

OTHER PUBLICATIONS

Office Action issued in Japanese Patent Application No. 2019-558272, dated Jul. 19, 2022.
International Preliminary Report on Patentability in International Application No. PCT/JP2018/044879 dated Jun. 9, 2020.
Notice of Reasons for Refusal in Japanese Patent Application No. 2019-558272, dated Feb. 28, 2023.

* cited by examiner (*1) MAIN INJECTION CONDITION (*2) INJECTION PRELIMINARY
OPERATION CONDITION

| CONTRAST MEDIUM | 90 | 80 | 70 | ... | 50 | ... | 10 |
|---|---|---|---|---|---|---|---|
| PHYSIOLOSICAL SALINE | 10 | 20 | 30 | ... | 50 | ... | 90 |

(a)

(b)

PRIOR ART

CHEMICAL LIQUID INJECTOR

This application is the U.S. National Phase under 35 U.S.C. § 371 of International Application No. PCT/JP2018/044879, filed Dec. 6, 2018, designating the U.S., and published in Japanese as WO 2019/111995 on Jun. 13, 2019, which claims priority to Japanese Patent Application No. 2017-235796, filed Dec. 8, 2017, the entire contents of which are incorporated herein by reference.

TECHNICAL FIELD

The present invention relates to a chemical liquid injector which injects a chemical liquid into a patient, and in particular, relates to a chemical liquid injector which enables to prevent a delay in injection caused due to an operation of a unidirectional valve in the chemical liquid circuit and a kink generated in a chemical liquid circuit.

BACKGROUND ART

Medical imaging diagnosis apparatuses include CT apparatuses, MRI apparatuses, angiography apparatuses, PET apparatuses, MRA apparatuses, and diagnostic ultrasonic imaging apparatuses. When capturing a medical image by using these apparatuses, for improving a contrast effect, a chemical liquid such as a contrast medium and a physiological saline is often injected into a patient. A chemical liquid to be injected is filled in a syringe in many cases, and moreover, the chemical liquid filled in the syringe is injected automatically according to injection conditions that have been set in advance by using a chemical liquid injector. In injection of the chemical liquid, for connecting the syringe mounted in the chemical liquid injector and the patient, a chemical liquid circuit is formed by components such as a catheter, an indwelling needle, and various tubes.

Patent Literature 1 discloses an injection head A110 of two-cylinder type as shown in FIG. 14. The injection head A110 includes a housing A113 in which two recesses A114 holding two syringes A200C and A200P are formed. A number of operation buttons A116 are disposed on an upper surface of the housing A113, and a sub-panel A115 is provided to a housing side portion according to the requirement. The syringes A220C and A220P include a cylinder member A210, and a piston member A220 inserted into the cylinder member A210. One syringe A200C is filled with a contrast medium and the other syringe A200P is filled with a physiological saline. A piston driving mechanism A130 is a mechanism for moving the piston member A220.

A chemical liquid circuit A230 is connected to the syringes A200c and A200P. The chemical liquid circuit A230, in this example, has a unidirectional valve A240 in a circuit portion that is to be connected to the syringe A200C filled with the contrast medium, and another unidirectional valve A250 in a circuit portion that is to be connected to the syringe A200P filled with the physiological saline, disposed therein.

PRIOR ART DOCUMENT

Patent Literature

Patent Literature 1: Japanese Patent No. 5800713

SUMMARY OF THE INVENTION

Problems to be Solved by the Invention

Although omitted in the diagram, a mechanism of chemical liquid injection in the chemical liquid circuit having a unidirectional valve as described above is as follows. As an initial state, a valve element of the unidirectional valve is at a predetermined closed position (or is in a predetermined initial form), and accordingly, the circuit is assumed to be blocked. From this state, as the piston member of the syringe is pushed by operating the piston driving mechanism, a pressure on the chemical liquid in the syringe rises up. Thereafter, as the pressure of the chemical liquid rises to a certain degree, the vale element of the unidirectional valve moves to an open position (or is deformed to a predetermined form), and an open-valve state is assumed. Thereafter, the chemical liquid in the syringe flows toward the patient through the unidirectional valve.

Regarding such series of operations, for changing from the closed-valve state to the open-valve state, it is necessary to apply a certain pressure to the valve element, and opening the unidirectional valve smoothly is important for realizing a responsive chemical liquid injection. Moreover, a similar problem, without being restricted to a case in which the unidirectional valve has been provided, may arise similarly even in a case in which, a kink of relatively moderate level is generated in a tube of the circuit for example, and when a certain volume of pressure is applied, the kink is eliminated.

Therefore, an object of the present invention is to provide a chemical liquid injector which enables to prevent a delay in injection caused due to an operation of a unidirectional valve in a chemical liquid circuit and a kink generated in the chemical liquid circuit.

Means for Solving the Problems

A chemical liquid injector according to an aspect of the present invention for achieving the abovementioned object is as follows:

The chemical liquid injector includes
a: a driving mechanism which applies a pressure to a chemical liquid in a container, and pushes out the chemical liquid; and
b: a control unit for setting operating conditions of the driving mechanism, wherein
the control unit comprises
a main injection condition determination unit which determines injection conditions for a main injection, and
an injection preliminary operation condition determination section which determines injection conditions for an injection preliminary operation, and
is configured to execute the injection preliminary operation and the main injection consecutively in this order when injecting the chemical liquid.

(Definition of Terminology)

'Chemical liquid circuit' refers to a flow path for circulating (distributing) a chemical liquid, to be connected to a syringe for injecting the chemical liquid into a blood vessel of a patient. The chemical liquid circuit includes at least one tube through which the chemical liquid flows, and various components attached to the tube. The chemical liquid circuit may include a catheter to be inserted into a blood vessel of the patient, or an indwelling needle to be tapped into a blood vessel of the patient. For enabling to inject a plurality of chemical liquids, the chemical liquid circuit may have a configuration in which, a front-end side to be connected to the catheter or the indwelling needle and a tail-end side which is the opposite side, are branched into a plurality by a combination of a plurality of tubes. The chemical liquid circuit, according to the configuration at the time of use, can be classified into an 'extracorporeal circuit portion' in which the entire chemical liquid circuit is located outside the body of a patient, and an 'internal circuit portion' in which at least a part of the chemical liquid circuit is located inside the body. According to this classification, the catheter or the indwelling needle belongs to the internal circuit portion, and members other than the catheter and the indwelling needle belong to the extracorporeal circuit portion. Consequently, it can be said that the 'chemical liquid circuit' includes at least the extracorporeal circuit portion out of the internal circuit portion and the extracorporeal circuit portion.

Specific examples of 'contrast medium' are (i) a contrast medium having an iodine concentration of 240 mg/ml (for example, a viscosity 3.3 mPa s at 37° C. and a specific gravity 1.268~1.296), (ii) a contrast medium having an iodine concentration of 300 mg/ml (for example, a viscosity 6.1 mPa·s at 37° C. and a specific gravity 1.335~1.371), (iii) a contrast medium having an iodine concentration of 350 mg/ml (for example, a viscosity 10.6 mPa s at 37° C. and a specific gravity 1.392~1.433), and the like. Note that, a contrast medium having an iodine concentration of 370 mg/ml or higher can also be used.

Specific examples of 'physiological saline' are, a physiological saline (for example, a viscosity 0.9595 mPa·s at 20° C. and a specific gravity 1.004~1.006) in which 180 mg of sodium chloride is contained in 20 mL of a physiological saline, and the like.

'injection protocol' is a protocol indicating as to what type of chemical liquid, with how much volume, and at which rate is to be injected. 'Injection rate' may be constant or may vary according to time. In a case of injecting a plurality of types of chemical liquids such as a contrast medium and a physiological saline, information such as an order of injecting the chemical liquids is also included in the injection protocol. As the injection protocol, a known arbitrary injection protocol can be used. Even regarding a procedure for preparing the injection protocol, a known procedure can be used. The injection protocol may include the maximum permissible value of an injection pressure (pressure limit). In a case in which the pressure limit has been set, the injection pressure is monitored during the injection operation, and an operation of the piston driving mechanism is controlled in order that the injection pressure does not exceed the pressure limit that has been set.

A piston driving mechanism which pushes out a chemical liquid inside the syringe is an example of the 'driving mechanism'. Alternatively, a pump mechanism which pushes out a chemical liquid in a container such as a chemical liquid bag or a bottle is an example of the 'driving mechanism'.

'Control unit' is an instrument which includes one or a plurality of processors and carries out arithmetic processing, and may be an independent instrument or may have been provided as a part of another apparatus.

Effects of the Invention

According to the present invention, it is possible to provide a chemical liquid injector which enables to prevent a delay in injection caused due to an operation of a unidirectional valve in a chemical liquid circuit and a kink generated in the chemical liquid circuit.

EMBODIMENT FOR CARRYING OUT THE INVENTION

An embodiment of the present invention will be described below while referring to the accompanying diagrams. Although an injection head of a so-called two-cylinder type is described in the following example, the present invention is not limited to the injection head of two-cylinder type.

[Chemical Liquid Injector and System]

Figure 1:
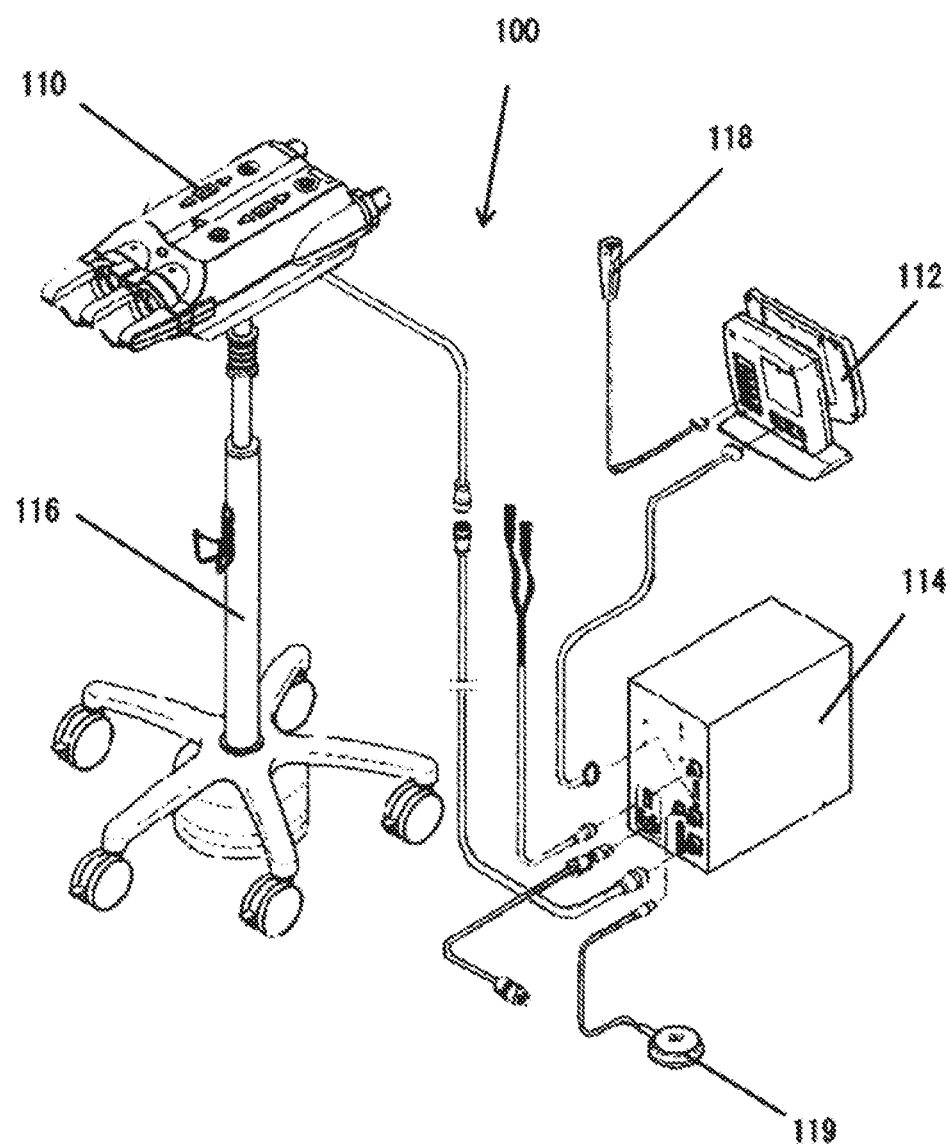
FIG. 1 is a perspective view showing an appearance of a chemical liquid injector according to an embodiment of the present invention.
Figure 3:
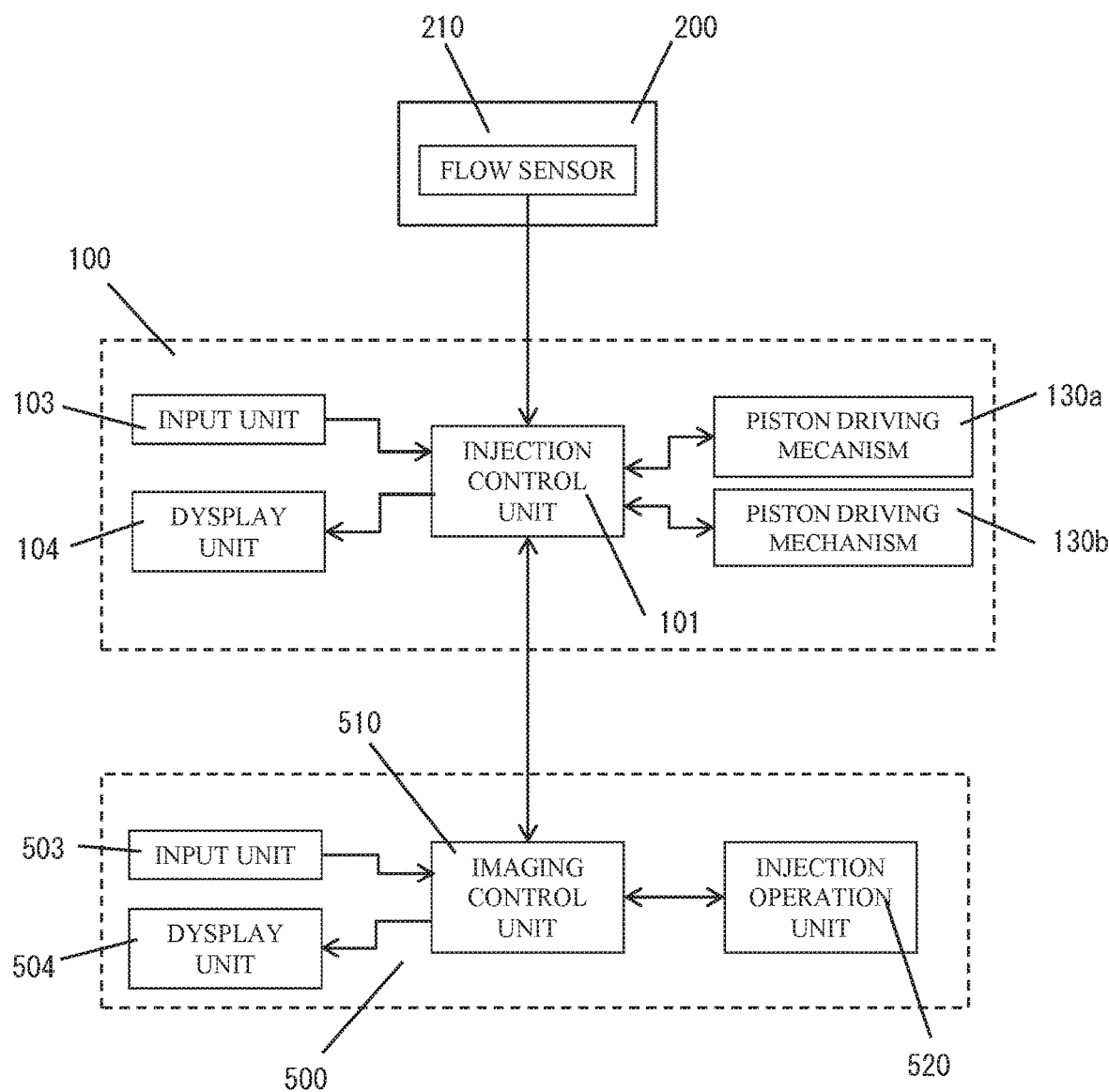
FIG. 3 is a block diagram of a system according to one embodiment of the present invention.

A chemical liquid injector 100 in FIG. 1 is an apparatus for angiography which is used at the time of angiographic examination. The chemical liquid injector 100 includes an injection head 110, a console 112, and a main unit 114. This chemical liquid injector 100 is to be used as a part of a system as shown in FIG. 3. The system in FIG. 3 includes the chemical liquid injector 100, a chemical liquid circuit 200 connected thereto, and an imaging apparatus 500.

(Injection Head)

As shown in FIG. 1, the injection head 110 and the console 112 are connected to the main unit 114. The injection head 110 and the console 112 are configured to be able to transmit and receive predetermined information mutually. The injection head 110, in this example, is rotatably supported by an upper portion of a stand 116. In other configuration (not shown), the injection head 110 may have been supported by a turning arm fixed to a ceiling.

Figure 2:
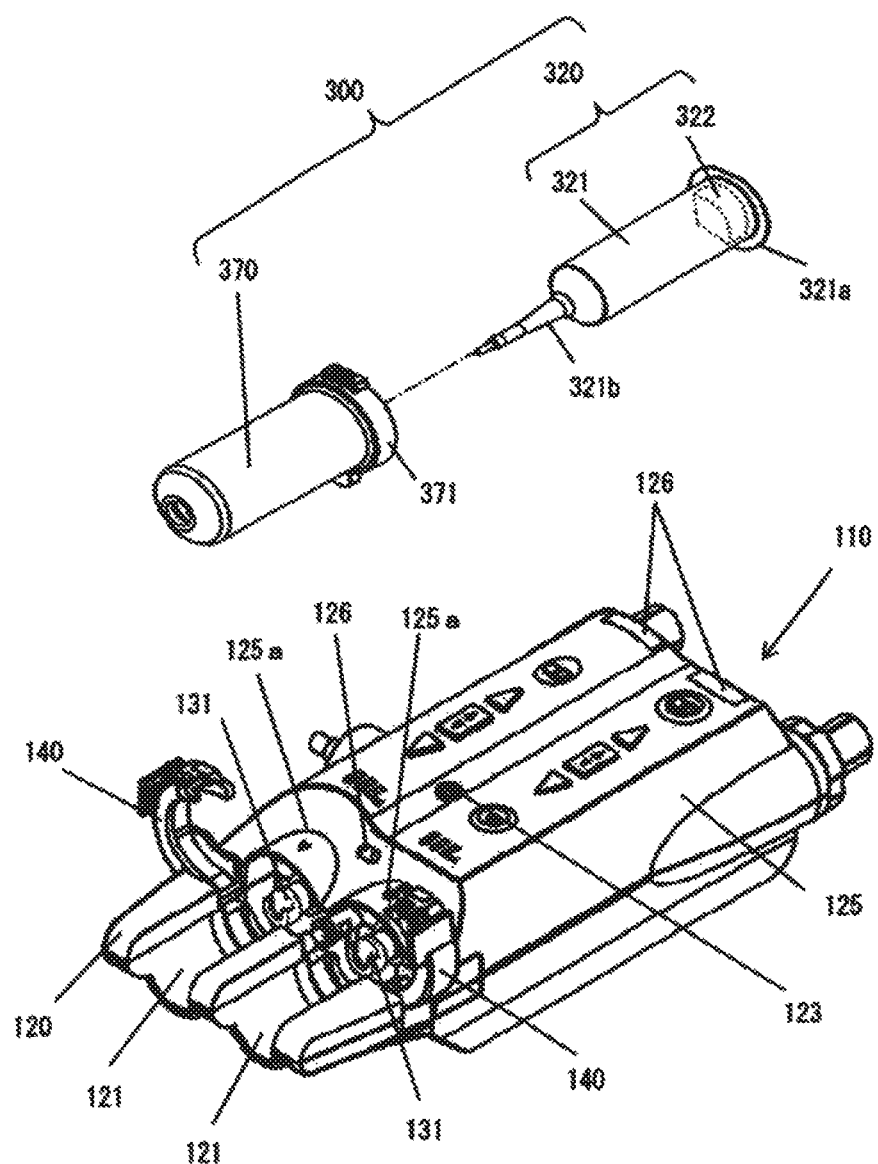
FIG. 2 is a perspective view showing an injection head shown in FIG. 1, together with a syringe to be mounted thereon.

The injection head 110, specifically, may have a configuration as in FIG. 2. In other words, the injection head 110 includes a pair of piston driving mechanisms 130a and 130b (also refer to FIG. 3) in this example. Each of the piston driving mechanisms 130a and 130b is driven independently for moving a piston 322 of a syringe 320 (details of the syringe will be described in detail later) back and forth.

Each of the piston driving mechanisms 130a and 130b (see FIG. 3), as shown in FIG. 2, has a ram member 131, and moreover, also has a driving source (not shown) such as a motor for moving the ram member 131 back and forth. The ram member 131 is configured to hold a protrusion (details to be described later) formed at a rear end of the piston 322.

Here, the syringe 320 and a protective cover 370 will be described (see FIG. 2). This syringe 320 is a called as a rod less syringe in general, and has a cylinder 321 and a piston 322. A nozzle portion 321b is formed at a front end of the cylinder 321. Moreover, a flange 321a is formed at a rear end of the cylinder 321. The piston 322 is inserted to be able to move back and forth inside the cylinder 321, and a protrusion (omitted in the diagram) which is held (or latched) by a part of the piston driving mechanism is formed at a rear end thereof.

The protective cover 370 is put on the syringe 320 to cover the syringe 320. The syringe 320 is mounted on the injection head 110 in a state of being inserted into the protective cover 370. The protective cover 370, as a whole, is a substantially circular cylindrical shaped member. An inner-diameter dimension of the protective cover 370 is such that when the cylinder 321 is inserted, there is almost no gap between the protective cover 370 and an outer peripheral surface of the cylinder 321.

An opening portion through which the nozzle portion 321b of the syringe 320 passes is formed at a front end of the protective cover 370. The syringe 320 is held in a state of the nozzle portion 321b protruded through the opening portion. A cover flange 371 is formed at a rear end of the protective cover 370. A recess formed to be contour-shaped to receive the flange 321a of the cylinder 321 is formed on an end surface (not shown) of the cover flange 371.

A contrast medium has a relatively high viscosity, and furthermore in angiography, an inner diameter of a catheter in general is less than 1 mm (for example) which is extremely thin. Therefore, at the time of chemical liquid injection, an extremely high internal pressure is generated in the cylinder 321. The protective cover 370 plays a role of preventing deformation or rupture due to expansion of the cylinder 321. Therefore, it is preferable that the protective cover 370 is formed of a material and to have a thickness that impart strength enabling to withstand adequately the internal pressure acting on the cylinder 321 during injection of a chemical liquid.

In the abovementioned description, although the protective cover 370 is used, the syringe 320 may be directly mounted on the injection head 110.

Referring again to FIG. 2, a front-end portion of the injection head 110 is provided with a syringe support 120 and a clamper 140. The syringe support 120 is a syringe mounting portion on which the syringe 320 having the protective cover 370 mounted thereon is placed. The syringe support 120 is located on a front-end side of the clamper 140, and has two recesses 121 to receive an outer peripheral surface of the protective cover 370 respectively. The clamper 140 is openably supported with respect to the syringe support 120, and holds the cover flange 371 of each protective cover 370 separately.

Each syringe 320 is set in the recess 121 in a state of the nozzle portion 321 directed toward the front-end side, and is fixed to the injection head 110 by closing the clamper 140.

A shape of the housing (an outer cover) of the injection head 110 is not limited in particular. It may be, for example, an outer cover 125 covering the entire mechanism except a portion having the syringe support 120 and the clamper 140. Various buttons 123 and a light emitting portion 126 may be provided on the outer cover 125. The outer cover 125 may have a mark 125a for distinguishing the corresponding ram member 131, at a position corresponding to each ram member 131. The mark 125a may bean arbitrary mark such as a letter or a symbol, and in the present embodiment, alphabets 'A' and 'B' are used.

(Chemical Liquid Circuit)

Next, the chemical liquid circuit 200 will be described below while referring to FIG. 4 and other diagrams. The chemical liquid circuit 200 forms a liquid path connecting the syringe and the patient.

The chemical liquid circuit 200 may include at least one tube, at least one connector, and a flow sensor according to the requirement. Specifically, the chemical liquid circuit 200, as shown in FIG. 4, may include tubes 201, 202, and 203, and a connector 204 which connects the tubes 201, 202, and 203. This circuit, as a whole, has a form in which two liquid paths are merged into one in mid-course.

The tubes 202 and 203 have at end portions thereof; connectors 205 and 206 respectively, for connecting to the syringe 320 (see FIG. 2). The tube 201 has at an end portion thereof, a connector 207 for connecting to a catheter (internal circuit portion). The chemical liquid circuit 200 may further include internal circuit portions such as a catheter or an indwelling needle. The catheter or the indwelling needle may be connected by the connector 207.

At least one of the connectors 205 and 206 connected to the first tubes 202 and 203 respectively may have a unidirectional valve. The unidirectional valve has a valve element which closes a flow path by being activated by a back pressure of a liquid, and has a function of preventing a reverse flow of a liquid from a side of the chemical liquid circuit 200 to which the catheter etc. is connected toward a side of the chemical liquid circuit 200 to which the syringe is connected. Although it is not necessarily limited, the valve element of the unidirectional valve in the present embodiment is supposed to be a valve element which, in an initial state, is at a predetermined closed position (or has an initial form), and the circuit is closed by the valve element being at the predetermined closed position. Regarding the chemical liquid circuit, a circuit having no unidirectional valve is also used sometimes.

The chemical liquid circuit 200 may further have a flow sensor 210. The flow sensor 210 of which, description in detail is omitted, may have a conduit, and may output an electric signal in accordance with a movement of a liquid (chemical liquid) inside the conduit. On the basis of this output signal, the chemical liquid injector 100 detects a flowrate of the chemical liquid in real time. The chemical liquid injector 100 may be configured to calculate various items related to chemical liquids and the chemical liquid injector by using this detection result.

(Mixing Device)

Figure 4:
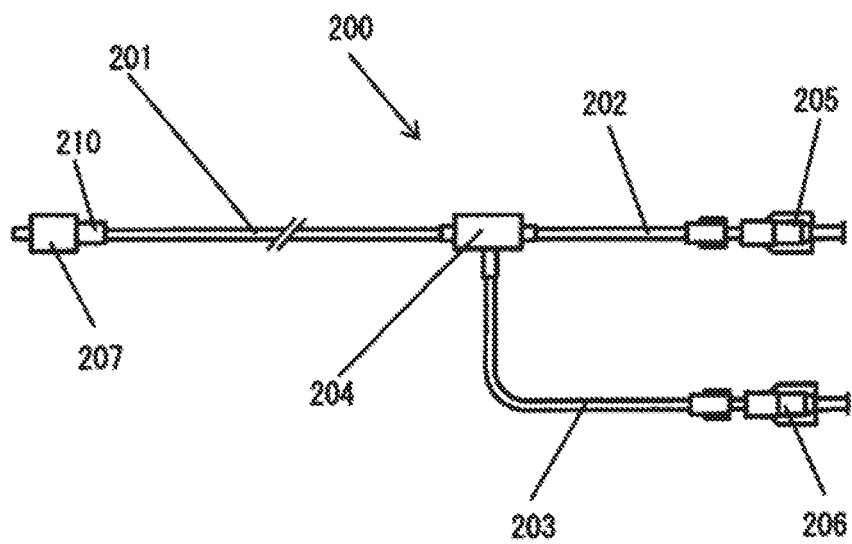
FIG. 4 is a diagram showing a configuration of a chemical liquid circuit shown in FIG. 1.
Figure 5:
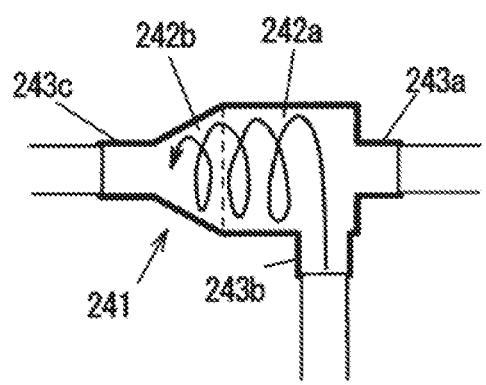
FIG. 5 is a schematic diagram of an example of a mixing device which may be included in the chemical liquid circuit.
Figure 6:
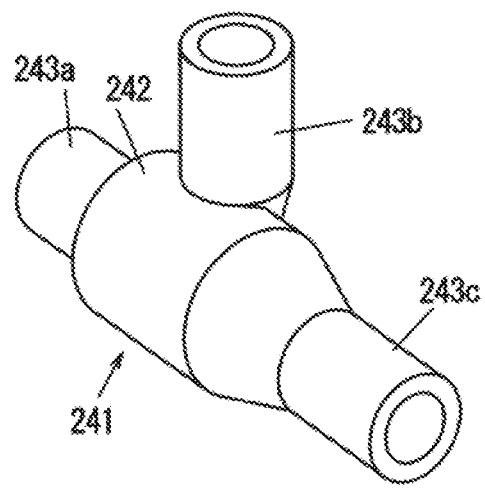
FIG. 6 is a perspective view of the mixing device shown in FIG. 5.
Figure 7:
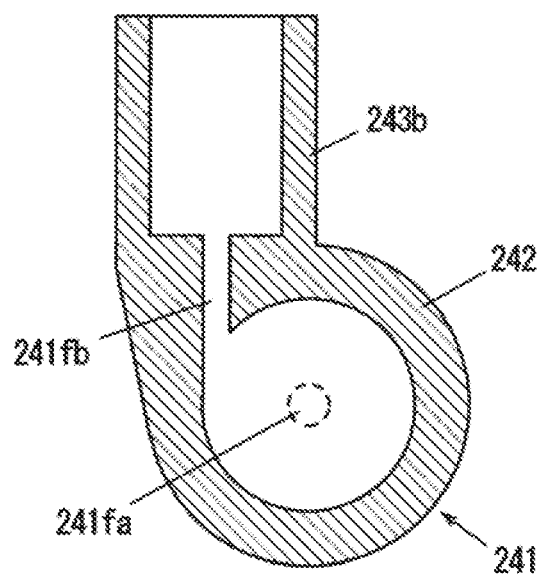
FIG. 7 is a cross-sectional view of the mixing device shown in FIG. 5.

In the chemical liquid circuit 200 in FIG. 4, the connector 204 which is commonly used was disposed at a merging portion. However, instead of the connector 204, a mixing device 241 as shown in FIG. 5 to FIG. 7 may be provided. The mixing device 241 includes a main-body portion 242 having a first chamber which is a swirl-flow generating chamber 242a generating a swirl flow and a second chamber which is a narrow chamber 242b converging the swirl flow in a radial direction.

In this example, the swirl-flow generating chamber 242a has a circular cylindrical shaped internal space, and the narrow chamber 242b has a conical-shaped internal space coaxial with the swirl-flow generating chamber 242a. For a cross-sectional shape in a lateral direction of the swirl-flow generating chamber, various shapes formed by curves other than a circle and an ellipse may be possible. Moreover, the swirl-flow generating chamber may have a narrow shape with a tip thereof narrowing gradually toward the narrow chamber.

A conduit portion 243a to which, one tube 202 is connected (see FIG. 2), is provided at an upstream side of a direction of flow of the main-body portion 242 of the mixing device 241, and a conduit portion 243c to which the tube 201 is (to be) connected (see FIG. 2) is provided at a downstream side of the direction of flow of the main-body portion 242. A conduit portion 243b to which, the tube 203 is (to be) connected (see FIG. 2) is disposed at a position somewhat on the upstream side of a center of the swirl-flow generating chamber 242a.

In this example, the contrast medium inflows through the conduit portion 243a and the physiological saline inflows through the conduit portion 243b, and both the liquids are mixed in the mixing device. Thereafter, a chemical liquid which is a mixture of the contrast medium and the physiological saline, outflows through the conduit portion 243c as a liquid outlet.

The conduit portion 243a through which a chemical liquid having a relatively high specific gravity inflows, on the upstream side of a direction of flow, is provided at a central portion of an upstream-side wall surface of the swirl-flow generating chamber 242a. The conduit portion 243c which is a liquid outlet is provided such that a center line of this conduit portion 243c and a center line of the conduit portion 243a are aligned (or in other words, both are coaxial). By disposing each portion to be coaxial, it is possible to improve an isotropy of a swirl generated in the mixing device. In other words, it is possible to generate the swirl evenly without stagnation in the space, and to improve a mixing efficiency.

On the other hand, the conduit 243b through which, a chemical liquid having a relatively low specific gravity inflows, is disposed on a side surface of the swirl-flow generating chamber 242a, and is extended in a tangential direction of a circumference of the swirl-flow generating chamber 242a having a circular cross sectional shape. To put in other words, the conduit portion 243b is provided at a position shifted toward a peripheral-edge side from a central-axis line of the circular-cylindrical space of the swirl-flow generating chamber 242a, and accordingly, a swirl flow of a chemical liquid having a lower specific gravity which has flowed through the conduit portion 243b is generated.

More elaborately, as shown in FIG. 7, a flow path 241fb is configured to be extended in a circumferential tangential direction of a curved inner surface of the swirl-flow generating chamber 242a, and accordingly, the chemical liquid flowed in through this plow path becomes a swirl flow. Furthermore, since the narrow chamber 242b, as evident also from the diagram, has an inner surface which is inclined to be narrowed toward the downstream side of the direction of flow, the swirl flow generated is converged in a central axial direction of the swirl.

Moreover, the conduit portion 243a through which the contrast medium inflows, communicates with the swirl-flow generating chamber 242a via a flow path 241fa. Accordingly, it is possible to infuse a chemical liquid having a high specific gravity into the swirl-flow generating chamber in a direction parallel to a central axis of the swirl flow of a chemical liquid having a low specific gravity. In other words, the chemical liquid having a high specific gravity is infused in a direction parallel to a central axis of the circular cylindrical space of the swirl-flow generating chamber. Moreover, the conduit portion through which the physiological saline inflows, communicates with the swirl-flow generating chamber via the flow path 241fb.

For example, an inner diameter of the flow path 241fb may be formed to be smaller than an inner diameter of the flow path 241fa through which the contrast medium inflows. According to such configuration, in a case of injecting a chemical liquid with a predetermined pressure, a flow rate of a chemical liquid having a low specific gravity which inflows through the flow path 241fb having a relatively smaller cross-sectional area becomes higher than a flow rate of a chemical liquid having a high specific gravity. Consequently, it is possible to prevent and suppress lowering of the mixing efficiency of chemical liquids caused due to attenuation of an inertial force of the swirl flow and an inadequacy of a swirling strength caused thereby, which may occur when the flow rate of a chemical liquid having a low specific gravity is slow.

In the mixing device 241 configured as described above, when a contrast medium and a physiological saline are allowed to inflow into the same device, the contrast medium flowed into the swirl-flow generating chamber through the flow path 241fa becomes a flow directed toward the downstream side of the axial direction. Whereas, the physiological saline flowed into the swirl-flow generating chamber through the flow path 241fb becomes a swirl flow swirling along a curved inner surface of the same chamber. And the swirl flow of the physiological saline is guided to the narrow chamber and is converged in a direction of a central axis of the swirl flow. Such swirl is known as Rankine swirl, and it is possible to converge the inertial force of the swirl flow near an axis of rotation of the swirl.

In a case of carrying out simultaneous injection of two chemical liquids by a chemical liquid circuit having such mixing device 241, the two chemical liquids are mixed favorably. In other words, in this example, it is possible to achieve a diluted contrast medium in which the contrast agent and the physiological saline are mixed favorably, and a contrast effect superior to that as compared to a case of a commonly-used chemical liquid circuit having a connecter in a mixing portion of chemical liquids is anticipated.

(Console and Main Unit)

The console 112 and other components of the chemical liquid injector 100 will be described below by referring again to FIG. 1 and FIG. 3. The console 112, for example, is configured as a device which includes an input unit 103 and a display device 104 (refer to FIG. 3). The console 112, in one aspect, has a touch-panel display, and this corresponds to the abovementioned input unit 103 and the display device 104.

The main unit 114 has a power supply unit (not shown), and an electric power is supplied to the injection head 110 and the console 112 from this power supply unit. An injection control unit 101 shown in FIG. 3 may be disposed inside the main unit 114 or may be disposed inside the console 112. Alternatively, some of the functions may be provided to the console 112 and some other functions may be provided to the injection head 110.

(Switches)

The chemical liquid injector 100 may further have a hand switch 118 and/or a foot switch 119 as an option. The hand switch 118 may have an operation button, and may be used for controlling a start and stop of an injection operation such that an operation of injecting chemical liquids by the injection head 110 is carried out only when the operation button is being pressed. As the hand switch 118, a switch having an operation button for carrying out an input which varies in multiple stages or consecutively (variable hand switch) may be used, or it may be a switch in which the injection rate is changed by an operation of this switch. The foot switch 119, in a case of carrying out a test injection for example, may be used for controlling a start and stop of an injection operation such that the operation of injecting chemical liquids by the injection head 110 is carried out only when the foot switch 119 is being pressed by foot.

(Arrangement for Operation of Injection Head)

The injection control unit 101 carries out an operation in the following manner for example:
- sets injection conditions (conditions for main injection) such as the injection volume and the injection rate of a chemical liquid by using at least some of data that has been input from the input unit 103,
- controls an operation of the piston driving mechanisms 130a and 130b in order that chemical liquids are injected through the syringe according to the injection conditions determined,
- controls a display of the display device 104,
- determines injection conditions for 'injection preliminary operation' that will be described later in detail.

The injection control unit 101 can be configured by including a so-called computer, and has a CPU, a ROM, a RAM, and an interface with other instruments. A computer program is installed in the ROM. The CPU, by executing various functions corresponding to the computer program, controls an operation of each component of the chemical liquid injector. The injection control unit 101 may have a graphical user interface (in other words, may have a function of displaying a GUI on the display device) for setting the injection conditions. Data of the GUI is stored in a predetermined storage area.

The input unit 103 is used for inputting data that is used for determining the injection conditions for a chemical liquid in the injection control unit 101. The input unit 103 may be a device such as a keyboard and/or a mouse for example. Data input from the input unit 103 is transmitted to the injection control unit 101, and data to be displayed on the display device 104 is transmitted from the injection control unit 101.

The display device 104 is controlled by the injection control unit 101 and carries out a display of data necessary for determining the injection conditions of a chemical liquid, a display of an injection protocol, a display of an injection operation, and a display of various warnings. The display device 104 may be a known display apparatus such as a liquid-crystal display apparatus.

(Imaging Apparatus)

The imaging apparatus 500, as shown in FIG. 3, includes an imaging operation unit 520 which executes an imaging operation, and an imaging control unit 510 which controls an operation of the imaging operation unit 520. The imaging apparatus 500 is capable of acquiring medical images including tomographic images and/or three-dimensional images of a patient into which chemical liquids are injected by the chemical liquid injector 100.

The imaging operation unit 520, normally, has an electromagnetic wave irradiation unit which irradiates electromagnetic waves to a bed for the patient and to a predetermined space on the bed. The imaging control unit 510 controls operation of the overall medical imaging apparatus such as determining imaging conditions and controlling an operation of the imaging operation unit 520 according to the imaging conditions that have been determined.

The imaging control unit 510 can be configured by including a so-called computer, and has a CPU, a ROM, a RAM, and an interface with other instruments. A computer program for controlling the medical imaging apparatus 500 is installed in the ROM. The CPU, by executing various functions corresponding to the computer program, controls an operation of each component off the medical imaging apparatus 500.

The chemical liquid injector 100 and the medical imaging apparatus 500 may be connected mutually to transmit and receive data between each other. The connection between the chemical liquid injector and the medical imaging apparatus may be a wired connection or a wireless connection.

The medical imaging apparatus 500 may further include a display unit 504 such as a liquid-crystal display which displays imaging conditions and medical images acquired, an input unit 503 such as a keyboard and/or a mouse for inputting the imaging conditions. At least some of data to be used for determining the imaging conditions is input from the input unit 503, and is transmitted to the imaging control unit 510.

Data to be displayed on the display unit 504 is transmitted from the imaging control unit 510. Moreover, it is also possible to use a touch panel having a touch screen disposed as an input unit on a display of the display unit, as the input unit 503 and the display unit 504. A part of the input unit 503, the display unit 504, and the imaging control unit 510 may be incorporated in one housing as a console for the medical imaging apparatus.

(Operation of Chemical Liquid Injection in the Present Embodiment)

An operation of the chemical liquid injection in the present embodiment will be described below while referring to FIG. 8 and FIG. 9.

Figure 8:
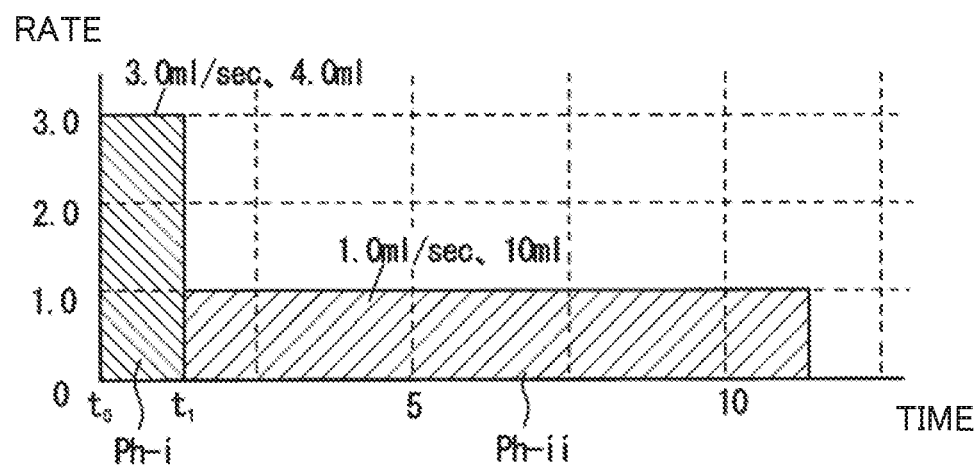
FIG. 8 is a diagram showing an injection control in which an injection preliminary operation is carried out prior to a main injection.
Figure 9:
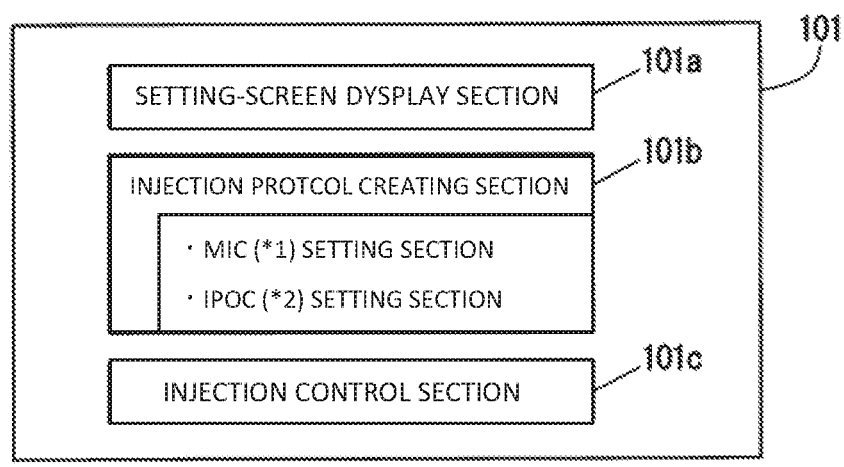
FIG. 9 is a diagram showing functional sections (units) which a control unit may have.

As shown in FIG. 8, the chemical liquid injection of the present embodiment is configured to carry out an injection preliminary operation phase Ph-i in the beginning, and subsequently, to carry out a main injection operation Phase Ph-ii. The injection preliminary operation phase Ph-i is a phase of injection with an object of eliminating kink or opening the unidirectional valve. The main injection operation phase Ph-ii is a phase of injecting a chemical liquid with conditions set as an injection protocol, in accordance with an imaging part and a body condition of the patient.

A time of the injection preliminary operation phase Ph-i is to be set to be extremely short. It is preferable that the injection time is 2.0 seconds or less, 1.5 seconds or less, and 1.0 seconds or less according to one aspect, for example. Moreover, it is preferable that the injection time is not less than 0.3 seconds or 0.5 seconds, according to one aspect. Specifically, a range of the injection time of the injection preliminary operation may be let to be 0.5 second-2.0 seconds, or 0.7 seconds to 1.5 seconds (a~b refers to not less than a and not more than b).

In the injection preliminary operation phase, the injection may be executed at a fixed (constant) injection rate. It is preferable that the injection rate is 2.0 ml/sec or more, 3.0 ml/sec or more, 4.0 ml/sec or more, and 5.0 ml/sec or more according to one aspect.

In terms of a relationship with the main injection, the rate in the injection preliminary operation is set higher than the rate of the main injection, or the injection time is set to be shorter than the injection time of the main injection.

Detailed conditions of the injection preliminary operation depend on a material and a size of the syringe, a volume remained of a chemical liquid, a diameter of the catheter (for example 2.1 Fr, 2.5 Fr), and a type of the chemical liquid. However, in a case of a chemical liquid injection in which a micro catheter (here, a catheter having a diameter not more than 2.5 Fr) is used, the realistic injection rate and injection volume are restricted to some extent. Therefore, it is preferable that an arrangement has been made such that the conditions (injection time and injection volume) for the injection preliminary operation can be calculated automatically from a predetermined calculating formula or table, and coefficients prepared in advance in accordance with the realistic injection rate and injection volume.

The injection rate for the injection preliminary operation, for example, can be calculated by the following calculating formula:

$$y_a = ax + by + c$$

here, $y_a$: an injection rate for the injection preliminary operation x: an injection rate set for the main injection y: volume of chemical liquid remained in syringe a, b, c: constants The injection rate ($y_a$) for the injection preliminary operation increases in accordance with the injection rate for the main injection. The relation may be such that, for example, when the injection rate for the main injection is 1.0 ml/sec, the injection rate for the injection preliminary operation is 3.0 ml/sec, when the injection rate for the main injection is 2.0 ml/sec, the injection rate for the injection preliminary operation is 4.0 ml/sec, and when the injection rate for the main injection is 3.0 ml/sec, the injection rate for the injection preliminary operation is 5.0 ml/sec.

The injection volume for the injection preliminary operation can be calculated by the following calculating formula for example:

$$y_b = (k \cdot z + c_b)x_x + (k_b \cdot z + c_b)$$

here, $y_b$: the injection volume for the injection preliminary operation x: rate set for the main injection z: volume remained in the syringe $k_b$: coefficient (positive number, for example, 0.005~0.020)

$c_b$: constant (positive number for example, 0.3~0.5)

In each of the abovementioned calculation, values of parameters may be determined appropriately upon taking into consideration an iodine volume, concentration (consistency) of the contrast medium, and a size of the catheter. In a case of two-cylinder type (to be described in detail later), the injection volume may be calculated by the same formula for both the syringes. However, without limiting to this, the injection volume may be calculated by a different calculating formula and with different parameters.

Regarding the correction of the calculating formula, it is preferable to acquire information of light and shades of an image achieved as a result of angiography, and to carry out the correction of the calculating formula on the basis of the information acquired in order that more appropriate contrast effect is achieved. For instance, when the contrast is as strong as or stronger than a predetermined standard, the correction of the calculation formula is to be carried out to weaken the contrast effect. Inversely, when the contrast is excessively weaker than a predetermined standard value, the correction of the calculation formula is to be carried out to enhance the contrast effect. The injection result and the contrast image may be stored in a storage area of a predetermined server, and the correction as mentioned above may be carried out.

In an example in FIG. 8, for the injection preliminary operation phase Ph-i, the injection rate is 3.0 ml/sec and the injection volume is 4.0 ml (consequently, the injection time is approximately 1.3 seconds). The injection control shown in FIG. 8 is as if the injection preliminary operation phase Ph-i was inserted prior to the main injection phase Ph-ii. The main injection is executed consecutively after (without leaving an interval) the injection preliminary operation.

As explained heretofore, according to the injection control of the present embodiment which includes the injection preliminary operation Phase Ph-i prior to the main-injection phase Ph-ii, a ram advance operation at higher speed and in shorter time than that for the main injection is carried out in the injection preliminary operation phase, and it is possible to carry out a favorable chemical liquid injection with a high responsiveness by opening smoothly the unidirectional valve by a pressure of a chemical liquid that rose. Alternatively, in a case in which a moderate kink is generated, it is also possible to facilitate eliminating the kink.

(Control Unit)

A device which carries out a processing for setting conditions of the injection preliminary operation phase is not limited in particular and it may be any of devices accommodated in the injection head 110, the console 112, or other instrument. As shown in FIG. 9, the injection control unit 101 may include a setting-screen display section 101*a*, an injection-protocol creating section 101*b*, and an injection control section 101*c*.

Here, the injection-protocol creating section 101*b* may be configured to include a 'main-injection condition setting section' and an 'injection preliminary operation condition setting section'. The main-injection condition setting section determines injection conditions for the main injection. The injection preliminary operation condition setting section determines injection conditions for the injection preliminary operation. The condition setting in this case, as mentioned above, may be executed by using parameters of the injection conditions for the main injection and a calculation formula prepared in advance. The injection preliminary operation condition setting section is included in the injection-protocol creating section as an example in FIG. 9, and as a matter of course, may be included in the injection control section 101*c*. The setting-screen display section 101*a* corresponds to a function of displaying a graphical user interface for setting conditions. The injection control section 101*c* corresponds to a function of making the ram member advance in accordance with the injection conditions set and operation conditions for the injection preliminary operation determined automatically to deal with the injection conditions that have been set.

The conditions for the injection preliminary operation determined automatically can be expressed as a graph as shown in FIG. 8 for example and the contents may not be necessarily indicated in a display. In other words, the chemical liquid injector according to an aspect of the present invention may be configured such that, once an operator has determined the conditions for the main injection phase, the injection preliminary operation appropriate thereto is created automatically, and an operation to carry out the injection preliminary operation is executed prior to the main injection phase. By doing so, the operator is able to carry out the test without being aware of the injection preliminary operation.

For setting the conditions for the injection preliminary operation, predetermined coefficients and/or formulae may be prepared in advance, and the conditions may be determined automatically by referring to a table for example. Parameters may include a shape of the syringe (such as a diameter and a stroke), a shape of a needle and/or catheter (such as a diameter and a length), a volume remained of a chemical liquid (a current position of the ram member), a type and physical properties of the chemical liquid, and an elastic property of the syringe and/or the protective cover.

Various information for the condition setting (such as information related to the syringe and/or the chemical liquid in the syringe, and information of the patient) may be input by other various methods. For instance, it may be a method in which information is read from an information recording medium such as an RFID tag (IC tag), and input. The information recording medium may be provided to the syringe and/or the protective cover, or other auxiliary or component of the chemical liquid injector. As an instrument that reads the information from the information recording medium, it is possible to use a reader of the RFID tag (IC tag), and the reader may be provided to the injection head for example. Furthermore, it may be provided to other instrument. Alternatively, it may be prepared as an independent instrument. It is also possible to use an information recording medium such as a bar code instead, or in combination. In this case, a bar code reader is provided, and the bar code information is read by the same reader.

In FIG. 8, as the main injection, although only one phase of 1.0 ml/sec and 10 seconds is depicted for example, the present invention is not necessarily limited to only one phase. For instance, a predetermined hold state may be assumed after the abovementioned phase, and the subsequent phase (injection for a predetermined time at a constant rate) may be carried out once or repeatedly.

(Case of Dilution Injection)

In the injection head of the two-cylinder type as in FIG. 2, sometimes, the first chemical liquid and the second chemical liquid are injected simultaneously (dilution injection). In this injection, two contrast media having different concentration, or a physiological saline and a contrast medium are mixed in a predetermined proportion, and injected. The proportion of mixing, without being limited to 5:5, maybe 4:6 or 3:7, and depending on the situation, maybe 1:9 (nine parts of physiological saline for one part of contrast medium) or 9:1 in some cases.

In a case of injecting upon mixing a physiological saline and a contrast medium, a difference in the specific gravity of the chemical liquids being large, the chemical liquids are hard to be mixed. Therefore, using the abovementioned mixing device is useful in one aspect. When there is a delay in injection caused due to generation of kink or an operation of the unidirectional valve, there is a possibility that the time taken for the desired mixing state to be assumed is also becomes somewhat long. The abovementioned point becomes a problem not only in the mixing device disclosed in the present application but also in a circuit which carries out mixing by simply merging two liquids.

Figures 10, 11:
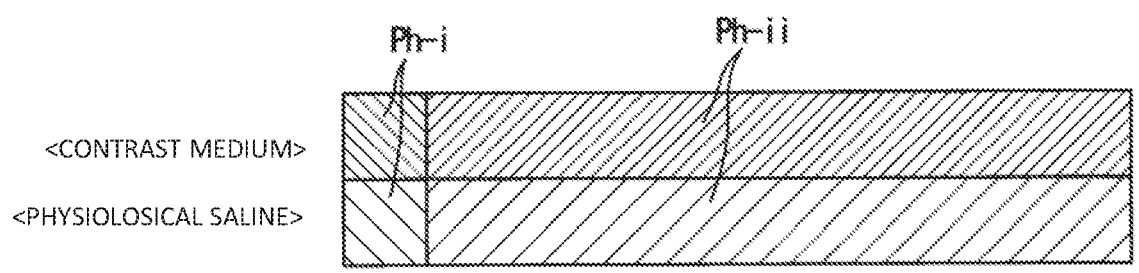
FIG. 10 is a diagram showing an example of the injection preliminary operation in a case of a simultaneous injection.
FIG. 11 is a table showing an example of a mixing proportion of a contrast medium and a physiological saline.

Therefore, in the present embodiment, even in a case of injecting simultaneously the first chemical liquid and the second chemical liquid, the injection preliminary operation phase mentioned in the embodiment described above is included in the injection conditions. As a specific example, as shown in FIG. 10, the injection preliminary operation phase Ph-i is set immediately prior to the main injection phase Ph-ii.

In this example, a contrast medium and a physiological saline are mixed in a proportion of 14%:86%. The injection conditions (injection rate, injection volume) for the main injection are as follows:

contrast medium 0.14 ml/sec, 4.2 ml
physiological saline 0.86 ml/sec, 25.8 ml

On the other hand, the injection conditions for the injection preliminary operation are same for the contrast medium and for the physiological saline, and are 2.5 ml/sec and 3.0 ml respectively. Even regarding the injection conditions for the injection preliminary operation in simultaneous injection, it is possible to determine automatically by using the calculating formulae described above. Note that, in accordance with a difference in the volume remained in the syringe, the conditions for the injection preliminary operation may have been set to be different for the contrast medium and for the physiological saline.

By carrying out such injection control, it is possible to carry out mixing of the chemical liquids favorably in the mixing device (or a normal connecter). As a result, particularly, even in an examination such as angiography in which a volume of liquid injected is comparatively small, it is possible to supply the chemical liquids mixed with a proportion closer to a mixing proportion that has been set, to a target part. Consequently, it is easy to achieve a desired contrast effect in angiography.

In the case of the two-cylinder type, the description will be supplemented with regard to the handling when the conditions for the injection preliminary operation differ for the first chemical liquid and the second chemical liquid. For instance, when the volume remained of the first chemical liquid is relatively small and a volume remained of the second chemical liquid is relatively large, a case in which, an operating time of the injection preliminary operation for the first liquid is short (for example, 0.5 seconds) and an operating time of the injection preliminary operation for the second liquid is long (for example 1.5 seconds), is envisaged.

In such case, it is preferable to carry out the subsequent chemical liquid injection based on the injection preliminary operation with the shorter injection time. In other words, in the specific example described above, after the injection preliminary operation for '0.5 seconds' is over, the simultaneous injection of the first chemical liquid and the second chemical liquid that has been set, is to be carried out consecutively. In such manner, by configuring to control the operation timing in accordance with the operation conditions with the short operating time, and to carry out the subsequent injection of the first chemical liquid and the second chemical liquid, it is possible to execute favorably the simultaneous injection of the first chemical liquid and the second chemical liquid with the desired conditions.

(Other Operation Examples)

Regarding the injection preliminary operation in the simultaneous injection, conditions for the injection preliminary operation phase of each chemical liquid may be set upon taking into consideration an ease of mixing the first chemical liquid (here, a contrast medium) and the second chemical liquid (here, a physiological saline). A processing as in the following description is also applicable to a case in which the volume of chemical liquid remained in both the syringes is about the same, or, to a case in which the volume of chemical liquid remained in both the syringes is different.

Specific example will be described below while referring to FIGS. 11-13. As shown in FIG. 1, for instance, in a case of mixing a contrast medium and a physiological saline with a proportion such as 90:10 to 70:30 (a case in which, the contrast medium is in relatively higher proportion), it is envisaged that the proper mixing of the two liquids may take time compared to a case in which the mixing proportion is 50:50. While it also depends on the tube and the connector used, and the viscosity of the contrast medium, the reason for this is the injection rate for the contrast medium is higher than the injection rate for the physiological saline, and the injection volume of the contrast medium becomes larger than the injection volume of the physiological saline.

Figure 12:
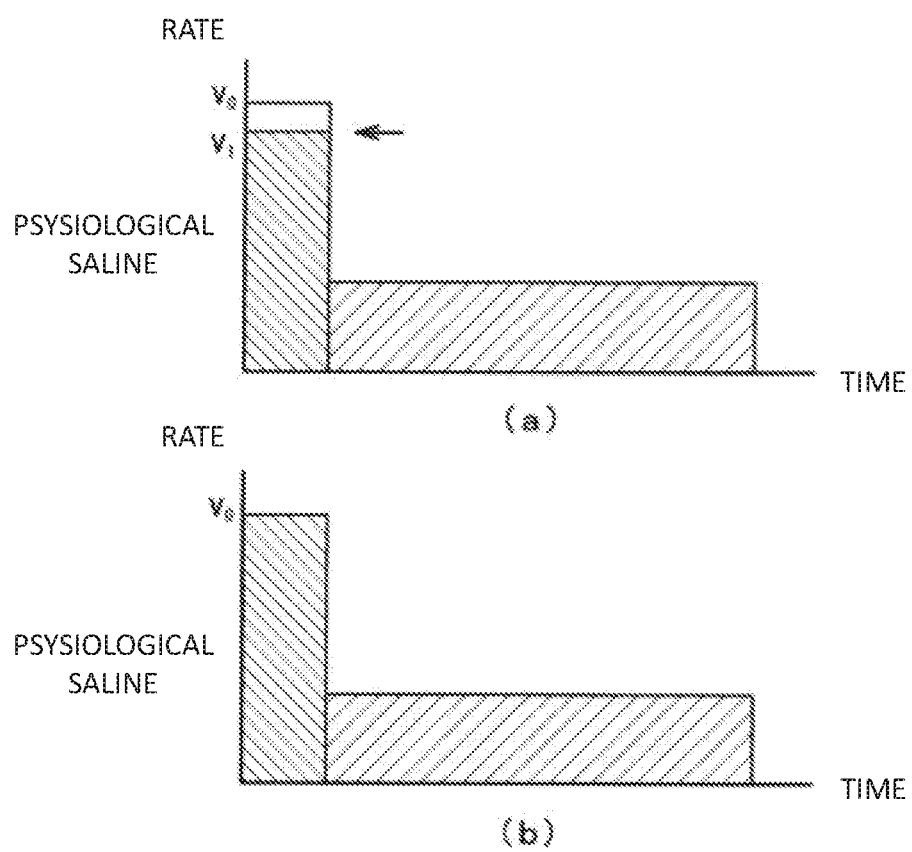
FIG. 12 is a diagram showing examples of conditions for an injection preliminary operation phase.

To deal with this, as an aspect of the present invention, as shown in FIG. 12, regarding the conditions for the injection preliminary operation of a contrast medium, the rate may be reduced from rate $v_0$ (same as the rate of the physiological saline in the injection preliminary operation) to rate $v_1$ for example. The specific value is not limited in particular, and the rate $v_1$ may be 90% or less than 90% of the rate $v_0$. On the other hand, it is preferable that the injection time is the same time in one aspect.

By letting the condition to be as abovementioned, even in a case of a mixed injection with the proportion of contrast medium relatively higher, it becomes possible to mix the two chemical liquids smoothly.

Although only the conditions of the contrast medium have been changed in the description above, processing in which (i) the rate of the physiological saline is increased, but the rate of the contrast medium is not changed, or (ii) the rate of the physiological saline is increased and the rate of the contrast medium is decreased may be carried out. Moreover, in the description heretofore, the rate of the contrast medium for the injection preliminary operation and the rate of the physiological saline for the injection preliminary operation (rate $v_0$) have been calculated in advance, and the description was made with the nuance of carrying out the rate change accordingly, but it is not necessarily limited to this. The rate corresponding to $v_1$ may be calculated directly by using a calculating formula or a table.

In the above, the example in which, the injection time for the injection preliminary operation is common and only the injection rate is changed, has been described. However, as an aspect of the present invention, the processing may be such that, the injection time is common and the injection rate is changed, or, both the injection rate and the injection time are changed. Moreover, in the abovementioned description, it was the example in which the rate of the contrast medium was changed to become relatively lower than the rate of the physiological saline, and conversely, the control may be carried out such that the rate of the physiological saline becomes relatively higher than the rate of the contrast medium.

Figure 13:
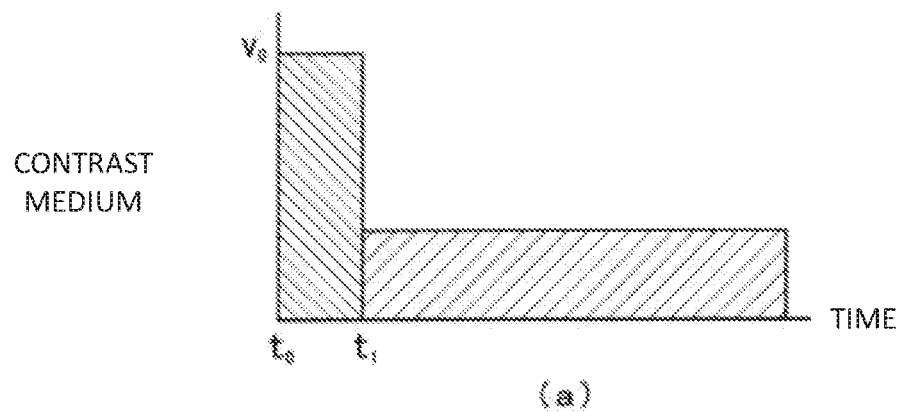
FIG. 13 is a diagram showing another example of conditions for the injection preliminary operation phase.
Figure 13:
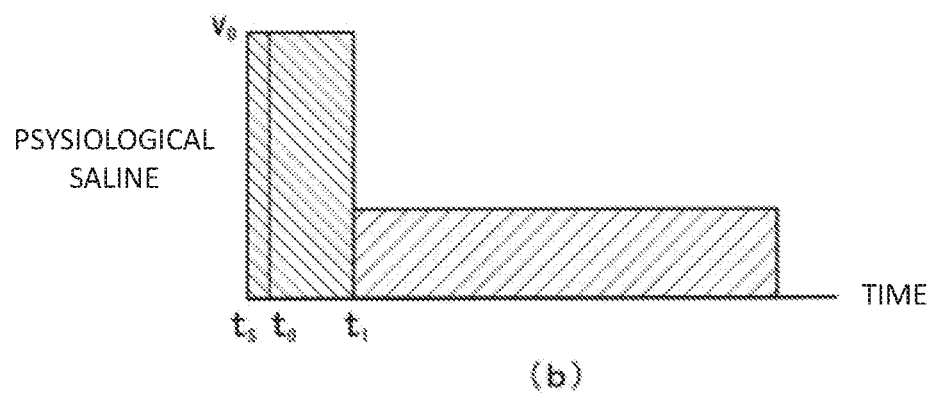
Figure 14:
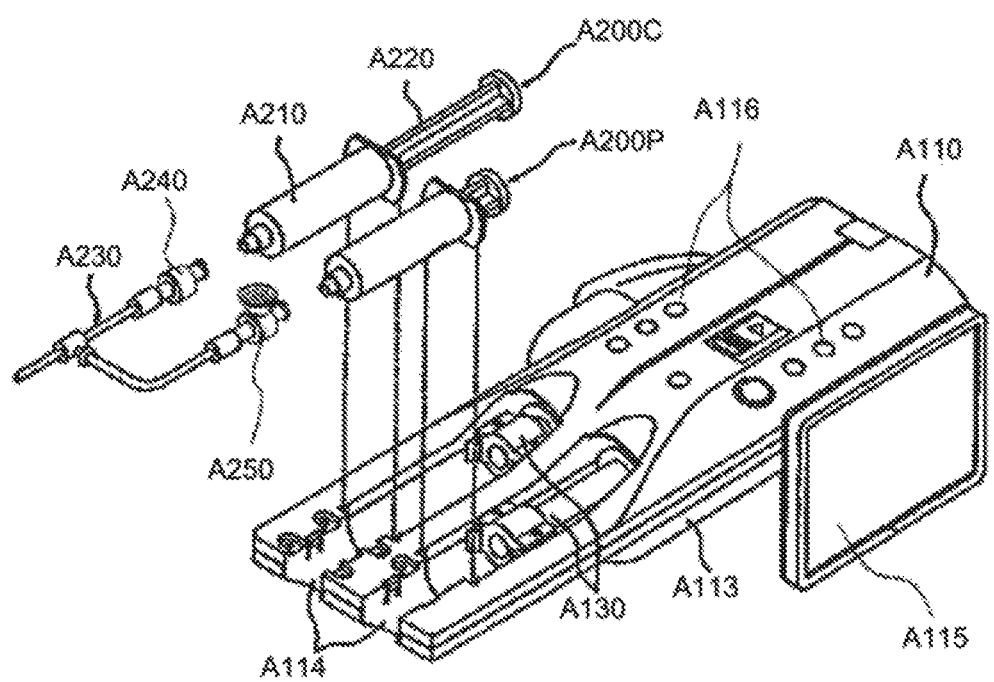
FIG. 14 is a diagram showing a conventional configuration example.

For instance, as in FIG. 13, after the start of the injection preliminary operation for the physiological saline, the injection preliminary operation for the contrast medium may be started after a predetermined delay (in the figure, time between time t, and to). In such manner, by making the injection time for the physiological saline slightly longer, an effect of the injection preliminary operation is improved, and as a result, even in a case of injecting with a proportion such as 90:10 to 70:30 (contrast medium:physiological saline) for example, it is possible to mix the contrast medium and the physiological saline favorably. Even in this case, according to one aspect, it is preferable that the timing (ti) for shifting to the main injection is same for the contrast medium and the physiological saline. In the abovementioned description, it was the example in which, injecting the contrast medium starts after starting to inject the physiological saline, and conversely. However, injecting the physiological saline may start after starting to inject the contrast medium.

Technical ideas disclosed heretofore can be used by combining appropriately. Moreover, in the embodiment described above, the explanation was made by citing an example of the chemical liquid injector for angiography. However, the technical idea of the present invention may be applied to a chemical liquid injector for CT examination. In a configuration for the CT examination, the injection pressure is not as high as that in angiography, and an injection head with a comparatively low motor output of the piston driving mechanism is to be used. Moreover, the protective cover of the syringe is also not to be generally used.

The chemical liquid injector of the present invention may be equipped with the following functions.
(1) Preliminary Operation Execution Mode As to whether the main injection is to be carried out upon executing the 'injection preliminary operation phase', or to be carried out without executing the 'injection preliminary operation phase' depends on a procedure of angiography, and a syringe and chemical liquids to be used. For instance, in angiography, particularly in a case of using a micro catheter, it is preferable that that the 'injection preliminary operation phase' is executed automatically. Such mode may be called as 'micro catheter mode' for example.

As a mounting of this function, for instance, a user interface (such as a graphical user interface) by which the chemical liquid injector 100 (refer to FIG. 1) receives an input from a user, may be provided. Specifically, the user makes an input for selecting a 'preliminary operation automatic-execution mode' to the console 112. This input is by selecting an icon for example (apart from this, may be by pressing a physical button). As the input is made, the chemical liquid injector 100 functions to carry out the main injection by executing the 'injection preliminary operation phase'.

The chemical liquid injector 100 may be configured such that information (such as French number) of a diameter of catheter to be used is input. The chemical liquid injector may be configured to determine the conditions for the injection preliminary operation by using that information, with the French number input as a parameter. For the input of the information, it is possible to use various inputs such as an input via touch panel display, an input by sound, and a gesture input by a movement of body. The information to be input may be one or a plurality of information of a manufacturer of the chemical liquid circuit, information of a model number, and information of a length.

(Supplemental Notes)

The present application discloses the following invention. Note that, reference numerals in brackets are assigned for reference, and are not intended for limiting the present invention.

1. A chemical liquid injector comprising:
   a: a driving mechanism (130) which applies a pressure to a chemical liquid in a container, and pushes out the chemical liquid; and
   b: a control unit (101) for setting operating conditions of the driving mechanism, wherein
      the control unit has
      a main-injection condition determination section which determines injection conditions for a main injection, and
      an injection preliminary operation condition determination section which determines injection conditions for an injection preliminary operation, and
      is configured to execute the injection preliminary operation and the main injection consecutively in the order when injecting the chemical liquid.
2. An injection rate of the chemical liquid for the injection preliminary operation is higher than an injection rate of the chemical liquid for the main injection.
3. An injection time for the chemical liquid in the injection preliminary operation is shorter than the injection time of the chemical liquid for the main injection.

4. The control unit (101) is configured to set automatically at least one parameter of the injection rate and an injection volume for the injection preliminary operation, on the basis of parameters of injection conditions for the main injection.

5. The control unit (101) is configured to set automatically both parameters of the injection rate and the injection volume for the injection preliminary operation, on the basis of parameters of injection conditions for the main injection.

6. The main injection includes a phase of carrying out an injection with a fixed injection rate and in a predetermined injection time.

7. The chemical liquid injector has a first piston driving mechanism (130*a*) which moves a piston member of a first syringe filled with a first contrast medium, provided to an injection head, and a second piston driving mechanism (130*b*) which moves a piston member of a second syringe filled with either a second contrast medium or a physiological saline, provided to the injection head, as the driving mechanism (130).

8. The chemical liquid injector further includes a chemical liquid circuit which is to be connected to the first syringe and the second syringe, wherein the chemical liquid circuit has a first liquid path to be connected to the first syringe, a second liquid path to be connected to the second syringe, a connector which is provided at a location where the first liquid path and the second liquid path merge, and a third path which extends from the connector.

9. The connector is a mixing device which mixes liquids by generating a swirl flow.

10. The control unit (101) is configured to set injection conditions for the injection preliminary operation by the first piston driving mechanism and injection conditions for the injection preliminary operation by the second piston driving mechanism.

11. When an operation time for one injection preliminary operation and an operation time for another injection preliminary operation differ, an operation timing of the first piston driving mechanism and an operation timing of the second piston driving mechanism are controlled in accordance with a shorter operation time.

12. The chemical liquid injector further includes one or a plurality of display devices, wherein the control unit does not display the injection conditions for the injection preliminary operation on one or the plurality of display devices.

1. 13. A method for controlling a chemical liquid injector comprising a driving mechanism which applies a pressure to a chemical liquid and pushes out the chemical liquid, and a control unit which controls an operation, the method comprising the steps of:
   a: determining injection conditions for an injection preliminary operation, by using parameters of injection conditions for a main injection, by a computer, and
   b: executing the injection preliminary operation and the main operation consecutively in this order.

14. An injection rate of a chemical liquid for the injection preliminary operation is higher than an injection rate of a chemical liquid for the main injection.

15. An injection time for a chemical liquid in the injection preliminary operation is shorter than the injection time for a chemical liquid in the main injection.

In the above description, it was an example in which an arithmetic processing is carried out by a console of the chemical liquid injector; however the arithmetic processing may be carried out by another entity (such as a computer which is a part of an imaging apparatus, or other computer). In this case, an aspect of the present invention can be expressed as follows:

A method of setting operating conditions for a driving mechanism which applies a pressure to a chemical liquid in a container and pushes out the chemical liquid, comprising:
   a: a step of determining injection conditions for an injection preliminary operation by using parameters of injection conditions for a main injection, by a computer.

The operating conditions (determining preliminary injection conditions) for the driving mechanism of the chemical liquid injector may be set in a predetermined computer, and the same computer may be configured to transfer those operating conditions to chemical liquid operating conditions.

The present application, heretofore, discloses the invention described as a category of method and a category of apparatus as aspects of the present invention, also expressed as an invention of a computer program. The computer program may activate a part of the chemical liquid injector (such as the console), or instead, may activate other instrument (computer). Moreover, it is possible to appropriately combine various technical features disclosed in the present application without departing from the scope of the invention.

DESCRIPTION OF REFERENCE NUMERALS

100 chemical liquid injector
101 control unit
103 input unit
104 display device
110 injection head
112 console
114 main unit
116 stand
121 recess
125 outer cover
130*a*, 130*b*(130) piston driving mechanism
131 ram member
140 clamper
200 chemical liquid circuit
201, 202, 203 tube
204 connector
210 flow sensor
241 mixing device
300 syringe assembly
320 syringe
321 cylinder
321*a* flange
322 piston
370 protective cover
371 cover flange
500 imaging apparatus
503 input unit
504 display device
510 imaging control unit
520 imaging operation unit

The invention claimed is:
1. A chemical liquid injector comprising:
   at least one driving mechanism which applies a pressure to a chemical liquid in at least one container, and pushes out the chemical liquid; and a control unit for setting operating conditions of the driving mechanism, wherein the control unit comprises:

a main-injection condition determination section which determines injection conditions for a main injection; and an injection preliminary operation condition determination section which determines injection conditions for an injection preliminary operation, and is configured to execute the injection preliminary operation and the main injection consecutively in this order when injecting the chemical liquid, and wherein an injection rate and an injection time of the injection preliminary operation are determined automatically using parameters including an injection rate in the main injection and a volume of the chemical liquid remaining in the container such that the injection rate in the injection preliminary operation is faster than the injection rate in the main injection, and the injection time in the injection preliminary operation is 2 seconds or less.

2. The chemical liquid injector according to claim 1, wherein the main injection includes a phase of carrying out an injection with a fixed injection rate and in a predetermined injection time.

3. The chemical liquid injector according to claim 1, wherein the chemical liquid injector comprises two driving mechanisms which apply a pressure to the chemical liquid in two containers, and pushes out the chemical liquid; wherein the at least one container is two syringes, one of the two driving mechanisms is a first piston driving mechanism which moves a piston member of a first syringe which is one of the two syringes filled with a first contrast medium, provided to an injection head; and the other of the two driving mechanisms is a second piston driving mechanism which moves a piston member of a second syringe which is another of the two syringes filled with one of a second contrast medium and a physiological saline, provided to the injection head.

4. The chemical liquid injector according to claim 3, further comprising:

a chemical liquid circuit which is to be connected to the first syringe and the second syringe, wherein the chemical liquid circuit comprises:

a first liquid path which is to be connected to the first syringe;

a second liquid path which is to be connected to the second syringe;

a connector provided at a location where the first liquid path and the second liquid path merge; and a third liquid path extending from the connector.

5. The chemical liquid injector according to claim 4, wherein the connector is a mixing device which mixes liquids by generating a swirl flow.

6. The chemical liquid injector according to claim 3, wherein the control unit is configured to set:

the injection conditions for the injection preliminary operation by the first piston driving mechanism; and the injection conditions for the injection preliminary operation by the second piston driving mechanism.

7. The chemical liquid injector according to claim 6, wherein when an operation time for one injection preliminary operation and an operation time for another injection preliminary operation differ, an operation timing of the first piston driving mechanism and an operation timing of the second piston driving mechanism are controlled in accordance with a shorter operation time.

8. The chemical liquid injector according to claim 1, further comprising:

one or a plurality of display devices, wherein the control unit does not display the injection conditions for the injection preliminary operation on one or the plurality of display devices.

9. A method for controlling a chemical liquid injector comprising a driving mechanism which applies a pressure to a chemical liquid and pushes out the chemical liquid, and a control unit which controls an operation, the method comprising:

automatically determining an injection rate and an injection time for an injection preliminary operation using parameters including an injection rate in a main injection and a volume of the chemical liquid remaining in a container such that the injection rate in the injection preliminary operation is faster than the injection rate in the main injection and the injection time in the preliminary injection operation is 2 seconds or less using a computer; and executing the injection preliminary operation and the main injection consecutively in this order.

* * * * *